(12) United States Patent
Adachi et al.

(10) Patent No.: US 11,263,886 B2
(45) Date of Patent: Mar. 1, 2022

(54) SHIP MANEUVERING ASSISTANCE SYSTEM, SHIP CONTROL DEVICE, SHIP CONTROL METHOD, AND PROGRAM

(71) Applicant: Furuno Electric Co., Ltd., Nishinomiya (JP)

(72) Inventors: Satoshi Adachi, Osaka (JP); Eisuke Sekine, Nishinomiya (JP); Katsuhiro Suzuki, Kobe (JP); Koji Atsumi, Takarazuka (JP); Daisuke Matsumoto, Kobe (JP)

(73) Assignee: Furuno Electric Co., Ltd., Nishinomiya (JP)

( * ) Notice: Subject to any disclaimer, the term of this patent is extended or adjusted under 35 U.S.C. 154(b) by 0 days.

(21) Appl. No.: 17/171,919

(22) Filed: Feb. 9, 2021

(65) Prior Publication Data

US 2021/0166546 A1  Jun. 3, 2021

Related U.S. Application Data

(63) Continuation of application No. PCT/JP2019/027084, filed on Jul. 9, 2019.

(30) Foreign Application Priority Data

Aug. 10, 2018  (JP) .............................. JP2018-151195

(51) Int. Cl.
| | |
|---|---|
| *G08B 21/06* | (2006.01) |
| *A61B 5/18* | (2006.01) |
| *B63B 79/40* | (2020.01) |
| *B63H 25/04* | (2006.01) |

(52) U.S. Cl.
CPC ................ *G08B 21/06* (2013.01); *A61B 5/18* (2013.01); *B63B 79/40* (2020.01); *B63H 25/04* (2013.01)

(58) Field of Classification Search
CPC ........ G08B 21/06; B63B 79/40; B60W 40/08; A61B 5/18; G08G 1/16; G08G 1/168
See application file for complete search history.

(56) References Cited

U.S. PATENT DOCUMENTS

| | | | |
|---|---|---|---|
| 5,689,241 A | 11/1997 | Clarke, Sr. et al. | |
| 7,228,233 B2* | 6/2007 | Kimura ................ | B60K 26/021 |
| | | | 701/301 |
| 8,665,113 B2* | 3/2014 | Arnold .................... | G01S 13/48 |
| | | | 340/907 |
| 9,955,925 B2* | 5/2018 | Kannan ................ | A61B 5/7264 |
| 10,039,445 B1* | 8/2018 | Torch ...................... | A61B 5/165 |
| 10,471,969 B1* | 11/2019 | Laserra Lima ... | B60W 60/0053 |

(Continued)

FOREIGN PATENT DOCUMENTS

| | | |
|---|---|---|
| JP | H10218095 A | 8/1998 |
| JP | 2001063694 A | 3/2001 |

(Continued)

*Primary Examiner* — Hoi C Lau
(74) *Attorney, Agent, or Firm* — Alleman Hall Creasman & Tuttle LLP

(57) ABSTRACT

In order to provide a ship maneuvering support system capable of coping with drowsiness of an operator, a ship maneuvering support system includes: a portable terminal carried by a ship's operator for detecting the operator's drowsiness, and a navigation device used for navigating the ship and performing a predetermined operation when the operator's drowsiness is detected.

18 Claims, 5 Drawing Sheets

(56) References Cited

U.S. PATENT DOCUMENTS

| | | | | |
|---|---|---|---|---|
| 2001/0028309 | A1* | 10/2001 | Torch | G01S 17/88 340/575 |
| 2001/0031930 | A1* | 10/2001 | Roizen | A61M 21/02 600/544 |
| 2003/0034902 | A1* | 2/2003 | Dickau | B64D 45/0031 340/945 |
| 2004/0094666 | A1* | 5/2004 | Rogitz | B64C 13/18 244/118.5 |
| 2008/0177197 | A1* | 7/2008 | Lee | A61B 5/18 600/545 |
| 2009/0021356 | A1* | 1/2009 | Galley | B60W 40/08 340/425.5 |
| 2009/0082956 | A1* | 3/2009 | Hamaguchi | G01C 21/26 701/408 |
| 2011/0105925 | A1* | 5/2011 | Hatakeyama | B60K 28/06 600/509 |
| 2011/0313259 | A1* | 12/2011 | Hatakeyama | B60K 28/06 600/300 |
| 2012/0143493 | A1* | 6/2012 | Tang | G01C 21/3407 701/423 |
| 2013/0162797 | A1* | 6/2013 | Bogner | G08B 21/06 348/78 |
| 2014/0132388 | A1* | 5/2014 | Alalawi | G09B 21/003 340/4.12 |
| 2014/0142798 | A1* | 5/2014 | Guarnizo Martinez | G08G 1/16 701/23 |
| 2014/0231166 | A1* | 8/2014 | Miller | B60W 40/08 180/272 |
| 2015/0015416 | A1* | 1/2015 | Kim | G08G 1/164 340/870.07 |
| 2015/0091716 | A1* | 4/2015 | Hathaway | G01S 7/22 340/435 |
| 2015/0094899 | A1* | 4/2015 | Hackenberg | B60W 50/082 701/23 |
| 2015/0142244 | A1* | 5/2015 | You | B60W 60/0053 701/23 |
| 2015/0203126 | A1* | 7/2015 | Kobana | B60K 28/06 701/93 |
| 2015/0351702 | A1* | 12/2015 | Kono | A61B 5/7278 600/549 |
| 2017/0080947 | A1* | 3/2017 | Boos | A61B 3/14 |
| 2017/0096236 | A1* | 4/2017 | Nelson | G05D 1/0055 |
| 2017/0108864 | A1* | 4/2017 | Wiklinska | B60W 60/0051 |
| 2017/0151959 | A1* | 6/2017 | Boesen | A61B 5/6803 |
| 2017/0153636 | A1* | 6/2017 | Boesen | G06F 1/163 |
| 2017/0235305 | A1* | 8/2017 | Jung | B60W 50/082 701/23 |
| 2017/0235306 | A1* | 8/2017 | Seki | B60W 40/08 701/23 |
| 2017/0242433 | A1* | 8/2017 | Ochiai | G01C 21/3484 |
| 2017/0285641 | A1* | 10/2017 | Goldman-Shenhar | B60W 50/082 |
| 2017/0327124 | A1* | 11/2017 | Kim | B60W 30/18 |
| 2017/0355377 | A1* | 12/2017 | Vijaya Kumar | B60W 40/08 |
| 2018/0157918 | A1* | 6/2018 | Levkova | G06K 9/4628 |
| 2018/0173230 | A1* | 6/2018 | Goldman-Shenhar | B60W 50/08 |
| 2018/0244288 | A1* | 8/2018 | Glaser | B60W 40/08 |
| 2019/0056731 | A1* | 2/2019 | Westbrook | G05D 1/0055 |
| 2019/0061772 | A1* | 2/2019 | Prinz | A61B 5/18 |
| 2019/0121356 | A1* | 4/2019 | Migneco | A61B 5/7264 |
| 2019/0294929 | A1* | 9/2019 | Yao | G06N 3/0454 |
| 2020/0101974 | A1* | 4/2020 | Ha | G01C 21/3492 |
| 2020/0130706 | A1* | 4/2020 | Rakshit | B60W 50/14 |
| 2020/0282984 | A1* | 9/2020 | Mizoguchi | G05D 1/0061 |
| 2020/0363220 | A1* | 11/2020 | Simoudis | G01C 21/3617 |
| 2020/0383580 | A1* | 12/2020 | Shouldice | B60W 40/08 |
| 2021/0123753 | A1* | 4/2021 | Liu | G01C 21/3415 |
| 2021/0166546 | A1* | 6/2021 | Adachi | B63B 43/20 |
| 2021/0290134 | A1* | 9/2021 | Talamonti | A61B 5/162 |
| 2021/0293948 | A1* | 9/2021 | Peng | G01S 13/536 |

FOREIGN PATENT DOCUMENTS

| | | |
|---|---|---|
| JP | 2005230030 A | 9/2005 |
| JP | 2007199025 A | 8/2007 |
| JP | 2017174091 A | 9/2017 |

* cited by examiner

SHIP MANEUVERING ASSISTANCE SYSTEM, SHIP CONTROL DEVICE, SHIP CONTROL METHOD, AND PROGRAM

CROSS-REFERENCE TO RELATED APPLICATION(S)

This application is a continuation of PCT International Application No. PCT/JP2019/027084, which was filed on Jul. 9, 2019, and which claims priority to Japanese Patent Application Ser. No. 2018-151195 filed on Aug. 10, 2018, the entire disclosures of each of which are herein incorporated by reference for all purposes.

TECHNICAL FIELD

The present invention relates to a ship maneuvering support system, a ship control device, a ship control method, and a program.

BACKGROUND

The U.S. Pat. No. 5,689,241 discloses a device for detecting and warning drowsiness of a driver of a vehicle.

SUMMARY

In pleasure boats and other ships, it is also required to take measures when an operator falls asleep.

An object of the present invention is to provide a ship operation support system, a ship control device, a ship control method, and a program capable of coping with drowsiness of an operator.

A ship maneuvering support system according to an aspect of the present invention comprises a portable terminal which is carried by a ship operator and detects the operator's drowsiness, and a navigation device which is used for navigation of the ship and performs a predetermined operation when the operator's drowsiness is detected.

A ship control device according to another aspect of the present invention includes: a communication means which is carried by a ship operator and receives drowsiness detection signal from a portable terminal which detects the drowsiness of the operator; and a control means which, when the drowsiness detection signal is received, causes a navigation device used for navigation of the ship to execute a predetermined operation.

A ship control device according to another aspect of the present invention includes: processing circuitry which accepts drowsiness from drowsiness detector carried by an operator of a ship when the drowsiness of the operator is detected; and performs a predetermined operation when the drowsiness of the operator is detected.

A ship control method according to another aspect of the present invention, drowsiness detection signal is received from a portable terminal which is carried by a ship operator and detects the drowsiness of the operator, and when the drowsiness detection signal is received, a navigation device used for navigation of the ship executes a predetermined operation.

A program according to another aspect of the present invention functions as a communication means which is carried by an operator of a ship and receives drowsiness detection signal from a portable terminal, which detects the drowsiness of the operator, and a control means which, when the drowsiness detection signal is received, causes a navigation device used for navigation of the ship to perform a predetermined operation.

According to the present invention, it is possible to cope with drowsiness of an operator.

BRIEF DESCRIPTION OF THE DRAWINGS

The illustrated embodiments of the subject matter will be best understood by reference to the drawings, wherein like parts are designated by like numerals throughout. The following description is intended only by way of example, and simply illustrates certain selected embodiments of devices, systems, and processes that are consistent with the subject matter as claimed herein:

DETAILED DESCRIPTION

Hereinafter, preferred embodiments of the present invention will be described with reference to the drawings. The following embodiments illustrate a method and apparatus for embodying the technical idea of the present invention, and the technical idea of the present invention is not limited to the following. The technical idea of the present invention can be modified in various ways within the scope of the claims.

Figure 1:
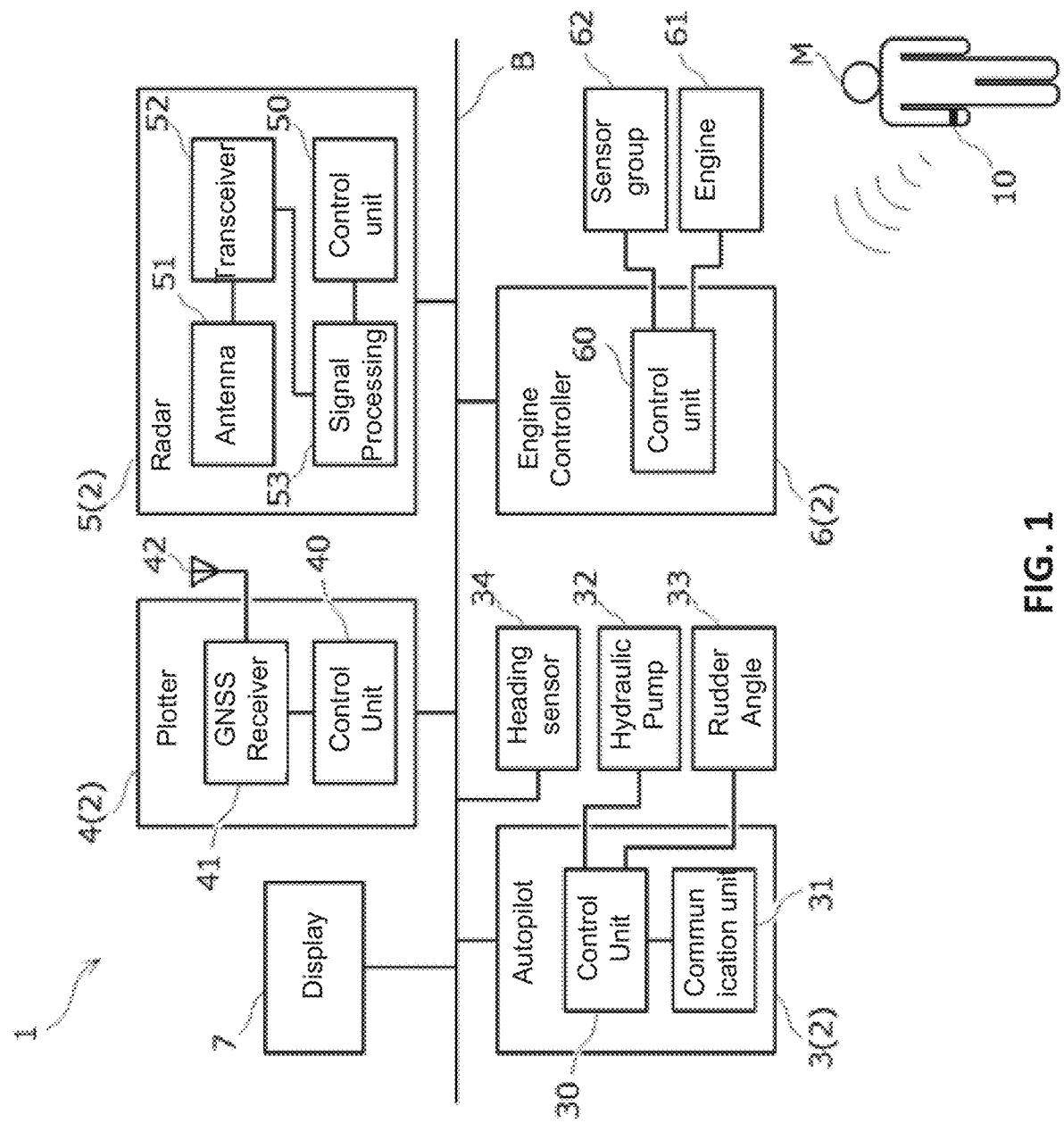
FIG. 1 is a block diagram illustrating an exemplary configuration of a ship maneuvering support system.

FIG. 1 is a block diagram showing an example of a configuration of a ship maneuvering support system 1. The ship maneuvering support system (1) is provided with a portable terminal (10) carried by a ship operator (M) (hereinafter also referred to as an operator M), and a plurality of navigation devices (2) used for navigation of a ship. The navigation devices (2) include an automatic steering device 3(2), a plotter 4(2), a radar 5(2), and an engine controller 6(2). The portable terminal (10) is hereinafter also referred to as drowsiness detector (10).

These navigation devices 2 are connected to a network B. The network B includes, for example, a CAN (Controller Area Network). A display 7 is also connected to the network B.

The drowsiness detector 10 is carried by the ship operator M of the ship and detects drowsiness of the ship operator M. The drowsiness detector 10 is attached to the ship operator M, for example. The drowsiness detector 10, when detecting the drowsiness of the operator M, transmits drowsiness detection signal to the navigation device 2.

In a ship, unlike a vehicle, an operator M sometimes leaves the operator's seat during navigation of the ship. Therefore, the drowsiness detector 10 needs to be carried by the operator M to enable the detection of the drowsiness of the operator M even when the operator M leaves the cockpit.

The drowsiness detector 10 is a wearable terminal such as a wristwatch type or a spectacle type. In an example, the drowsiness detector 10 corresponds to a smart watch. In another example, the drowsiness detector 10 corresponds to smart glasses. The drowsiness detector 10 includes, for example, a sensor for detecting the pulse wave of the operator M, and detects the drowsiness of the operator M based on the detected pulse wave. The drowsiness detector 10 may include, for example, a camera for photographing the eyes of the operator M, and may detect the drowsiness of the operator M based on the movement of the eyes or eyelids.

The drowsiness detector 10 is not limited to a wearable terminal to be attached to the operator M, but may be a portable terminal such as a smartphone stored in a pocket of the operator M's clothes or the like.

The drowsiness detector 10 may detect not only a complete sleep state but also a transition from an awake state to a sleep state as drowsiness. For example, the drowsiness level of the operator M may be evaluated, and if the drowsiness level exceeds a threshold value, it may be determined that the operator M is dozing.

The drowsiness detector 10 transmits drowsiness detection signal to the navigation device 2 using, for example, wireless communication such as Bluetooth (registered trademark). The navigation device 2 includes a communication unit 31 for wireless communication with the drowsiness detector 10. In the illustrated example, the communication unit 31 is included in the automatic steering device 3, but it is not limited thereto, and may be included in other navigation devices 2 and the like.

The automatic steering device 3 includes a control unit 30. The control unit 30 is connected to a hydraulic pump 32 for driving a steering gear of a ship and a rudder repeat back unit (rudder angle detector) 33 for detecting a steering angle of the steering gear. A heading sensor 34 detects the azimuth of the bow. The control unit 30 calculates a target steering angle for turning the direction of the bow to the target direction, and drives the hydraulic pump 32 so that the steering angle of the steering machine becomes the target steering angle.

The plotter 4 is provided with a control unit 40 and a GNSS receiver 41. The GNSS receiver 41 is connected to an antenna 42 and calculates the current position of the ship based on the radio wave received from the GNSS (Global Navigation Satellite System). The control unit 40 plots the present position of the ship on the chart image. The control unit 40 outputs a chart image in which the current position of the ship is plotted to the display 7 or its own display (not shown).

The plotter 4 supplies the target point set by the operator M on the chart image displayed on the display 7 or the like to the automatic steering device 3.

The radar 5 includes a control unit 50, an antenna 51, a transceiver 52, and a signal processing unit 53. The radio wave received by the antenna 51 is converted into a digital signal by the transceiver 52 and the signal processing unit 53, and supplied to the control unit 50. The control unit 50 generates a radar image representing the detected target on the basis of the acquired signal, and outputs the radar image to the display 7 or its own display unit (not shown).

The engine controller 6 includes a control unit 60. The control unit 60 is connected to an engine 61 as a power unit of a ship and a sensor group 62 provided in the engine 61. The sensor group 62 includes various sensors such as a rotation speed sensor, a throttle opening sensor, and an intake pressure sensor. The control unit 60 controls an electronic throttle, a fuel injection device, an ignition device, and the like of the engine 61.

The control unit 30, 40, 50, or 60 (also referred to as "processing circuitry") included in the navigation device 2 is an example of a ship control apparatus. The present invention is not limited thereto, and a ship control device may be provided separately from the navigation device 2.

The control unit 30, 40, 50, or 60 is a computer including a CPU, a RAM, a ROM, a nonvolatile memory, an input/output interface, and the like. The CPU executes information processing according to a program loaded into the RAM from the ROM or the nonvolatile memory. The program may be supplied via an information storage medium such as an optical disk or a memory card, or may be supplied via a communication network such as the Internet, for example.

Figure 2:
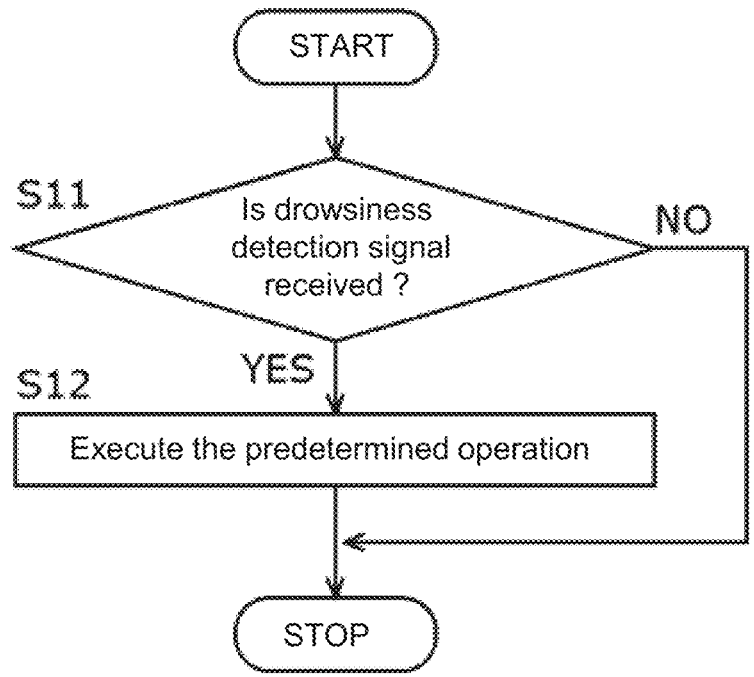
FIG. 2 is a flow diagram illustrating an exemplary procedure for a ship control method.

FIG. 2 is a flow chart showing a procedure example of a ship control method implemented by the control unit 30, 40, 50, or 60. When the control unit 30, 40, 50, or 60 receives the drowsiness detection signal from the drowsiness detector 10 (S 11: YES, Processing as Communication Means), it causes the navigation device 2 to execute the predetermined operation described below (Step 12: Processing as Control Means).

Unlike the operation of vehicles, there is no designated route in the operation of ships, and ships often navigate to designated destinations in the sea area or to specific directions using the autopilot function. However, if the operator M falls asleep in such a situation, the vessel will continue to navigate automatically without any monitoring or control by the operator M, and this will be a dangerous situation for the vessel itself and other vessels. Therefore, in the present embodiment, when the drowsiness of the operator M is detected, the navigation device 2 is made to perform a predetermined operation described below to add a predetermined restriction, thereby realizing navigation with consideration given to safety.

FIGS. 3A-3E are diagrams for explaining the operation of the automatic steering device 3 when drowsiness is detected. The automatic steering device 3 shifts to a predetermined pattern navigation when the drowsiness of the operator M is detected. The pattern navigation is set so that, for example, the overall travel distance or travel speed in the traveling direction C is smaller than that in the case where the ship S only travels in the traveling direction C. This enables the vessel to stay as long as possible in the position where the operator M was, when the operator's drowsiness was detected, thereby preventing collision with other vessels or other objects. In addition, by shifting to a pattern navigation in which the heading direction frequently changes, the ship S can be shaken more than when the drowsiness of the operator M is detected, so that the operator M can be urged to wake up quickly.

Figure 3A:
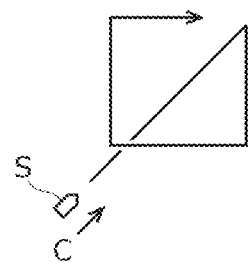
FIGS. 3A-3E are diagrams for explaining the operation of an automatic steering device when drowsiness is detected.
Figure 3B:
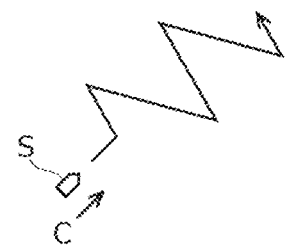
Figure 3C:
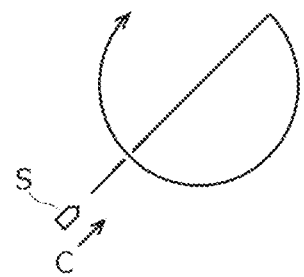
Figure 3D:
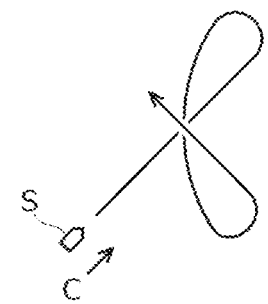
Figure 3E:
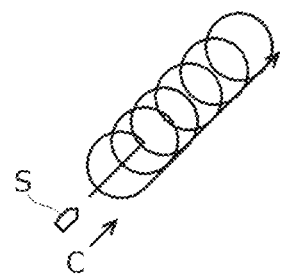

Specifically, the automatic steering device 3 may make the ship S navigate in a rectangular pattern as shown in FIG. 3A, may make the ship S navigate in a zigzag pattern as shown in FIG. 3B, may make the ship S navigate in a circular pattern as shown in FIG. 3C, may make the ship S navigate in a figure-8 pattern as shown in FIG. 3D, or may make the ship S navigate in a spiral pattern as shown in FIG. 3E.

Figure 4A:
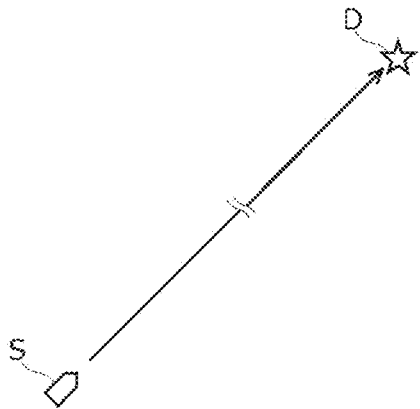
FIGS. 4A-4C are diagrams for explaining an operation of a plotter when drowsiness is detected.
Figure 4B:
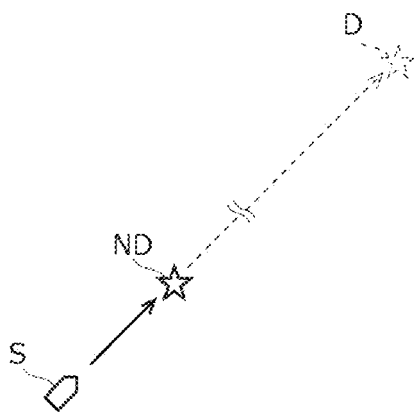
Figure 4C:
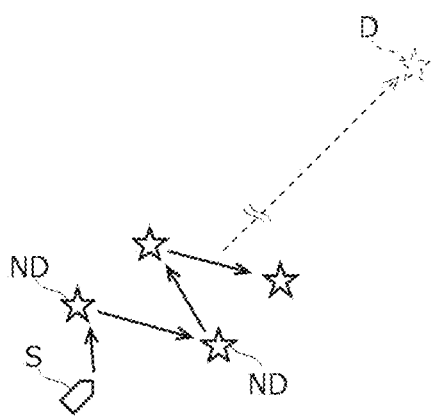

FIGS. 4A-4C are diagrams for explaining the operation of the plotter 4 when drowsiness is detected. The plotter 4 changes the target point D supplied to the automatic steering device 3 when the drowsiness of the operator is detected.

Specifically, as shown in FIG. 4A, when the drowsiness of the operator is detected while the ship S is navigating toward the target point D using the automatic steering device 3, the plotter 4 supplies the automatic steering device 3 with a position closer to the ship S than the previous target point D as a new target point ND.

As shown in FIG. 4C, the plotter 4 may supply a plurality of positions set between the target point D and the ship S as a new target point ND to the automatic steering device 3. The automatic steering device 3 controls the steering machine of the ship S so as to sequentially follow a plurality of new target points ND. This enables the ship S to stay as long as possible in the position where the operator was when the operator's drowsiness was detected, thereby preventing collision with other vessels or other objects.

However, the plotter 4 may also supply a new target point ND shown in FIG. 4B or 4C to the automatic steering device 3 and switch the steering mode of the automatic steering device 3 so as to navigate toward the new target point ND, even if the drowsiness of the operator is detected while the ship S is navigating on a constant course by using the automatic steering device 3.

Figure 5A:
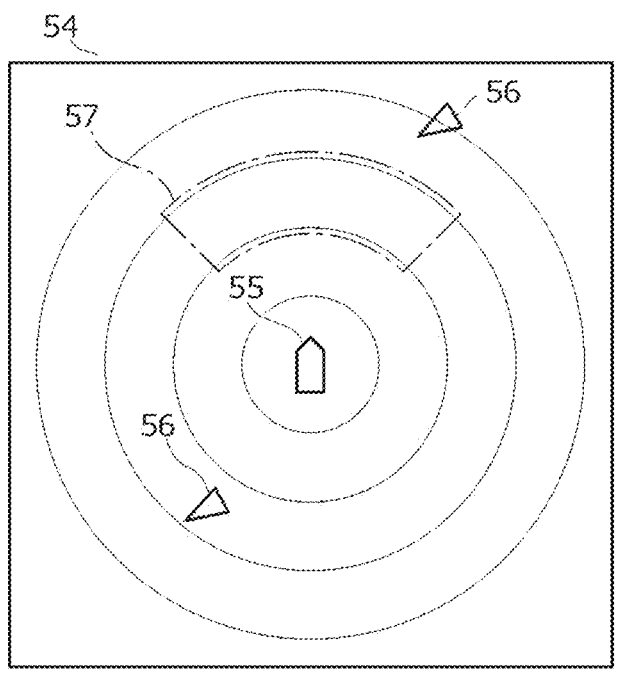
FIGS. 5A and 5B are diagrams for explaining an operation of a radar when drowsiness is detected.
Figure 5B:
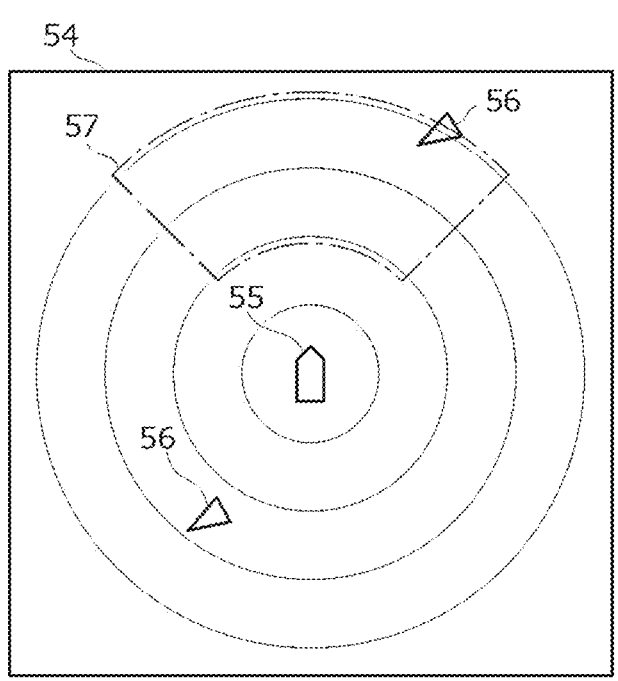

FIGS. 5A and 5B are diagrams for explaining the operation of the radar 5 when drowsiness is detected. FIG. 5A shows the radar image 54 before the drowsiness detection, and FIG. 5B shows the radar image 54 after the drowsiness detection.

In the center of the radar image 54, an own ship mark 55 representing the own ship is arranged. In the radar image 54, a target mark 56 indicating a target such as a detected other ship or a rock reef is arranged. In the radar image 54, a target monitoring range 57 for monitoring a target is set.

The target monitoring range 57 is, for example, located in front of the self-ship mark 55, and is formed in a fan shape extending in the lateral direction. When the target mark 57 enters the target monitoring range 56, the radar 5 outputs an alarm message to the display 7 or outputs an alarm sound from a speaker (not shown).

As shown in FIG. 5B, the radar 5 expands the target monitoring range 57 when the drowsiness of the operator is detected. Specifically, the target monitoring range 57 is expanded in front of the own ship mark 55 (Direction of travel of the vessel). It may be enlarged in the lateral direction. Thus, the alarm can be output from a stage earlier than the normal time.

The engine controller 6 reduces the output of the engine 61 when the drowsiness of the operator M is detected. For example, the output of the engine is reduced until the navigation speed of the vessel is reduced to a predetermined low speed such as a crawling speed (e.g., 8 km/h or less). This enables the ship S to stay as long as possible in the position where the operator M was when the operator's drowsiness was detected, thereby preventing collision with other vessels or other objects.

The operation of the automatic steering device 3, the plotter 4, the radar 5, and the engine controller 6 in the case where the drowsiness of the operator M is detected may be performed by any one of them or may be performed by combining two or more of them.

Further, the series of processes shown in FIG. 2 may be executed when the target mark 56 detected by the radar 5 is not included in the predetermined range based on the own ship mark 55 (For example, a circle having a predetermined radius around the ship mark 55), or may be executed when the automatic steering device 3 is performing autopilot.

When the target mark 56 detected by the radar 5 is within a predetermined range based on the own ship mark 55 and the drowsiness of the operator M is detected, a warning message may be outputted to the display 7 or a warning sound may be outputted from a speaker (not shown) to prompt the operator to M wake up quickly.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processor. A processor can be a microprocessor, but in the alternative, the processor can be a controller, microcontroller, or state machine, combinations of the same, or the like. A processor can include electrical circuitry configured to process computer-executable instructions. In another embodiment, a processor includes an application specific integrated circuit (ASIC), a field programmable gate array (FPGA) or other programmable device that performs logic operations without processing computer-executable instructions. A processor can also be implemented as a combination of computing devices, e.g., a combination of a digital signal processor (DSP) and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C. The same holds true for the use of definite articles used to introduce embodiment recitations. In addition, even if a specific number of an introduced embodiment recitation is explicitly recited, those skilled in the art will recognize that such recitation should typically be interpreted to mean at least the recited number (e.g., the bare recitation of "two recitations," without other modifiers, typically means at least two recitations, or two or more recitations).

It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.).

For expository purposes, the term "horizontal" as used herein is defined as a plane parallel to the plane or surface of the floor of the area in which the system being described is used or the method being described is performed, regardless of its orientation. The term "floor" can be interchanged with the term "ground" or "water surface." The term "vertical" refers to a direction perpendicular to the horizontal as just defined. Terms such as "above," "below," "bottom," "top," "side," "higher," "lower," "upper," "over," and "under," are defined with respect to the horizontal plane.

As used herein, the terms "attached," "connected," "mated" and other such relational terms should be construed, unless otherwise noted, to include removable, moveable, fixed, adjustable, and/or releasable connections or attachments. The connections/attachments can include direct connections and/or connections having intermediate structure between the two components discussed.

Numbers preceded by a term such as "approximately," "about," and "substantially" as used herein include the recited numbers, and also represent an amount close to the stated amount that still performs a desired function or achieves a desired result. For example, the terms "approximately," "about," and "substantially" may refer to an amount that is within less than 10% of the stated amount. Features of embodiments disclosed herein preceded by a term such as "approximately," "about," and "substantially" as used herein represent the feature with some variability that still performs a desired function or achieves a desired result for that feature.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A navigation system comprising:
   a portable terminal configured:
      to be carried by an operator of a ship; and
      to detect drowsiness of the operator; and
   one or more navigation devices used for navigation of the ship configured to perform a predetermined operation, upon detection of the drowsiness, wherein
   the one or more navigation devices include a plotter that is configured to supply a target point to an automatic steering device, and
   the plotter changes or newly supplies the target point when the drowsiness of the operator is detected.

2. The navigation system of claim 1, wherein
   the one or more navigation devices include the automatic steering device that is configured to shift to a predetermined pattern navigation when the drowsiness of the operator is detected.

3. The navigation system of claim 2, wherein
   the predetermined pattern is:
      a rectangular pattern;
      a zigzag pattern;
      a circular pattern;
      a figure-8 pattern; or
      a spiral pattern.

4. The navigation system of claim 1, wherein
   a distance of the new target point from the ship is less than that of a previous target point from the ship.

5. The navigation system of claim 1, wherein
   the one or more navigation devices include a radar that is configured to expand a target monitoring range in a radar image, for monitoring a target, when the drowsiness of the operator is detected.

6. The navigation system of claim 5, wherein
   the expanding the target monitoring range includes enlarging the target monitoring range in a lateral direction.

7. The navigation system of claim 1, wherein
   the one or more navigation devices
      include an engine controller connected to an engine of the ship; and
      are configured to reduce an output of the engine when the drowsiness of the operator is detected.

8. The navigation system of claim 5, wherein
   the one or more navigation devices are further configured to execute a predetermined operation when
      the target detected by the radar is not within a predetermined range with respect to the ship and
      the drowsiness of the operator is detected.

9. The navigation system of claim 1, wherein:
   the portable terminal is further configured to transmit drowsiness detection signal indicating detection of the drowsiness to the one or more navigation devices; and
   the one or more navigation devices are further configured to execute the predetermined operation upon receiving the drowsiness detection signal.

10. The navigation system of claim 9, wherein
    the portable terminal is further configured to:

determine drowsiness level of the operator; and
transmit the drowsiness detection signal when the drowsiness level exceeds a threshold value.

11. The navigation system of claim 1, wherein
the portable terminal is configured to detect at least one of:
   a complete sleep state of the operator, and
   a transition from an awake state to a sleep state of the operator.

12. The navigation system of claim 1, wherein
the portable terminal is:
   a smartphone;
   a wearable smart watch; or
   wearable smart glasses.

13. The navigation system of claim 1, wherein
the portable terminal is:
   a sensor for detecting a pulse wave of the operator; or
   a camera for capturing an image of eyes of the operator to detect the drowsiness based on the movement of eyes and eyelids of the operator.

14. A navigation device comprising:
processing circuitry configured:
   to accept drowsiness from drowsiness detector carried by an operator of a ship when the drowsiness of the operator is detected; and
   to perform a predetermined operation when the drowsiness of the operator is detected, wherein
the navigation device is a plotter that is configured to supply a target point to an automatic steering device, and
the plotter changes or newly supplies the target point when the drowsiness of the operator is detected.

15. The navigation device of claim 14, wherein
the automatic steering device is configured to shift to a predetermined pattern navigation when the drowsiness of the operator is detected.

16. A ship control method comprising:
receiving drowsiness detection signal from a portable terminal carried by an operator of a ship to detect the drowsiness of the operator; and
causing a navigation device used for navigation of the ship to execute a predetermined operation upon receiving the drowsiness detection signal,
causing the navigation device as a plotter to supply a target point to an automatic steering device, and
causing the navigation device to change or newly supply the target point when the drowsiness of the operator is detected.

17. The ship control method of claim 16, further comprising:
causing the automatic steering device to shift to a predetermined pattern navigation when the drowsiness of the operator is detected.

18. The ship control method of claim 17, wherein
the predetermined pattern is:
   a rectangular pattern;
   a zigzag pattern;
   a circular pattern;
   a figure-8 pattern; or
   a spiral pattern.

* * * * *